US00PP37179P2

(12) United States Plant Patent
van den Hoogen

(10) Patent No.: US PP37,179 P2
(45) Date of Patent: Dec. 30, 2025

(54) ***MENTHA* PLANT NAMED 'Allmefreshimp'**

(50) Latin Name: ***Mentha* x *piperita***
Varietal Denomination: Allmefreshimp

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 19/224,787

(22) Filed: May 31, 2025

(51) Int. Cl.
*A01H 5/02* (2018.01)
*A01H 6/50* (2018.01)

(52) U.S. Cl.
USPC ..... Plt./259

(58) Field of Classification Search
USPC ..... Plt./259, 263.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Mentha* plant named 'Allmefreshimp', characterized by its upright plant habit; relatively vigorous growth habit; freely basal branching habit; healthy and relatively small dark green-colored leaves; freely flowering habit; dense inflorescences with numerous light purple-colored flowers; and good postproduction longevity as a cut flower.

2 Drawing Sheets

Figure 1:
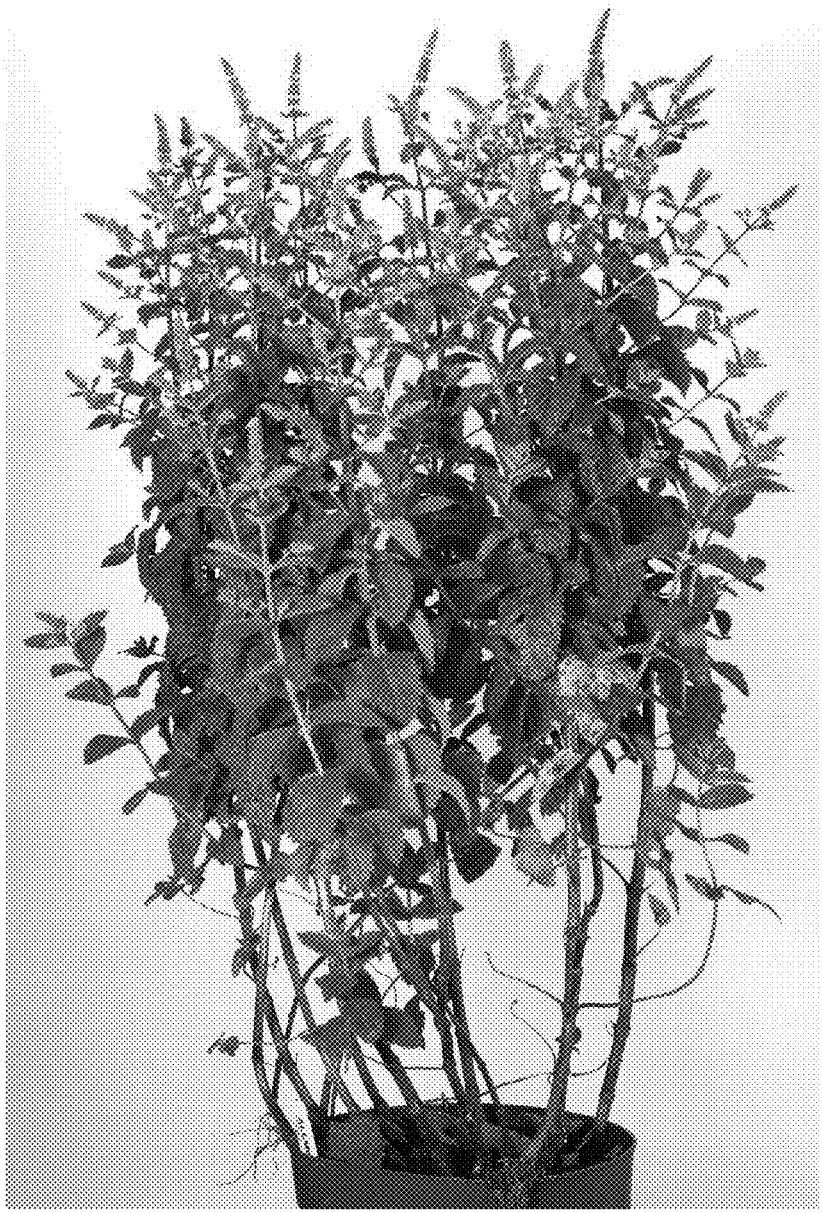

Botanical designation: *Mentha* x *piperita*.
Cultivar denomination: 'ALLMEFRESHIMP'.

CROSS-REFERENCED TO CLOSELY-RELATED APPLICATIONS

A European Community Plant Breeder's Rights application for the instant plant was filed by the Assignee, Allplants Holding B.V. of Cuijk, The Netherlands on Aug. 21, 2024, application number 2024/1998. Foreign priority is not claimed to this application.

BACKGROUND OF THE INVENTION

The present invention relates to a new and distinct cultivar of *Mentha* plant, botanically known as *Mentha* x *piperita*, commonly known as Peppermint, typically produced as a field-grown cut flower and hereinafter referred to by the name 'Allmefreshimp'.

The new *Mentha* plant is a product of a planned breeding program conducted by the Inventor in Cuijk, The Netherlands. The objective of the breeding program is to create new *Mentha* plants with healthy leaves and suitability as a cut flower.

The new *Mentha* plant originated from an open-pollination in August 2016 of a proprietary selection of *Mentha* x *piperita* identified as code number 51-2014-2-2, not patented, as the female, or seed, parent with an unknown proprietary selection of *Mentha* x *piperita* as the male, or pollen, parent. The new *Mentha* plant was discovered and selected by the Inventor as a single flowering plant from within the progeny of the stated open-pollination in a controlled nursery environment in Cuijk, The Netherlands in July 2017.

Asexual reproduction of the new *Mentha* plant by terminal stem cuttings in a controlled environment in Cuijk, The Netherlands, since September 2017 has shown that the unique features of this new *Mentha* plant are stable and reproduced true to type in successive generations.

SUMMARY OF THE INVENTION

Plants of the new *Mentha* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allmefreshimp'. These characteristics in combination distinguish 'Allmefreshimp' as a new and distinct *Mentha* plant:

1. Upright plant habit.
2. Relatively vigorous growth habit.
3. Freely basal branching habit.
4. Healthy and relatively small dark green-colored leaves.
5. Freely flowering habit.
6. Dense inflorescences with numerous light purple-colored flowers.
7. Good postproduction longevity as a cut flower.

Plants of the new *Mentha* differ primarily from plants of the female parent selection in flower color as flowers of plants of the new *Mentha* are more intense purple in color than flowers of plants of the female parent selection. In addition, leaves of plants of the new *Mentha* are smaller and darker green in color than leaves of plants of the male parent selection.

Plants of the new *Mentha* can be compared to plants of *Mentha* x *piperita* 'Allmestart', not patented. In side-by-side comparisons, plants of the new *Mentha* differ primarily from plants of 'Allmestart' in the following characteristics:

1. Stems of plants of the new *Mentha* that are exposed to sunlight are tinged with greyish brown whereas stems of plants of 'Allmestart' exposed to sunlight are greyish green in color.

2. Leaves of plants of the new *Mentha* are smaller than leaves of plants of 'Allmestart'.
3. Plants of the new *Mentha* flower about one week earlier than plants of 'Allmestart'.

BRIEF DESCRIPTION OF THE PHOTOGRAPHS

The accompanying colored photographs illustrate the overall appearance of the *Mentha* plant showing the colors as true as it is reasonably possible to obtain in colored reproductions of this type. Colors in the photographs may differ slightly from the color values cited in the detailed botanical description which accurately describe the actual colors of the new *Mentha* plant.

The photograph on the first sheet (FIG. 1) comprises a side perspective view of a typical flowering plant of 'Allmefreshimp' grown in a container.

Figure 2:
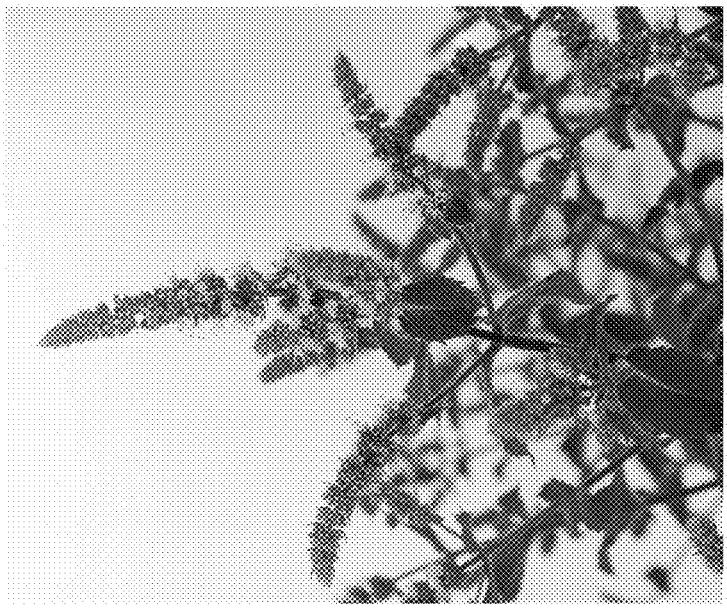

The photograph on the left side of the second sheet (FIG. 2) is a close-up view of a typical flowering plant of 'Allmefreshimp'.

Figure 3:
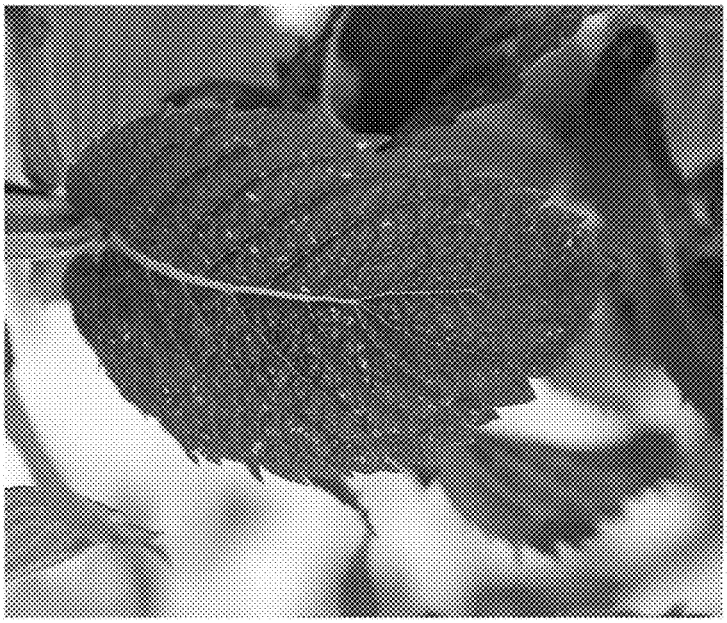

The photograph on the right side of the second sheet (FIG. 3) is a close-up view of a typical leaf of 'Allmefreshimp'.

DETAILED BOTANICAL DESCRIPTION

Plants used for the aforementioned photographs and following description were grown in ground beds and in 25-cm containers during the spring and summer in a outdoor nursery in Cuijk, The Netherlands and under cultural practices typical of commercial *Mentha* production. During the production of the plants, day temperatures ranged from about −10° C. to 35° C. and night temperatures ranged from about −10° C. to 25° C. Plants were one year old when the photographs and the description were taken. In the following description, color references are made to The Royal Horticultural Society Colour Chart, 2015 Edition, except where general terms of ordinary dictionary significance are used.

Botanical classification: *Mentha* x *piperita* 'Allmefreshimp'.

Parentage:

*Female, or seed, parent*.—Proprietary selection of *Mentha* x *piperita* identified as code number 50-2014-2-2, not patented.

*Male, or pollen, parent*.—Unknown proprietary selection of *Mentha* x *piperita*, not patented.

Propagation:

*Type cutting*.—Terminal stem cuttings.

*Time to initiate roots, summer*.—About ten days at temperatures ranging from about 10° C. to 25° C.

*Time to produce a rooted young plant, summer*.—About 15 to 25 days at temperatures ranging from about 10° C. to 25° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial suitable to be produced as field-grown cut flower.

*Plant and growth habit*.—Upright plant habit with numerous dense inflorescences; overall plant shape, narrowly obovate to broadly oblong; relatively vigorous growth habit and moderate to rapid growth rate.

*Plant height, soil level to top of foliar plane*.—About 81.5 cm.

*Plant height, soil level to top of floral plane*.—About 90.4 cm.

*Plant width*.—About 65.7 cm.

*Lateral branch description*.—Branching habit: Freely branching habit with about 16 primary branches and about 225 lateral branches developing per plant; pinching is not required to enhance lateral branching potential; leaves quadrilateral with distinct edges. Length (excluding inflorescence): About 14.7 cm. Diameter: About 3 mm. Internode length: About 3.7 cm. Strength: Relatively strong. Aspect: Primary branches, mostly erect; lateral branches about 50° to 70° from the primary branch axis. Texture and luster: Densely pubescent; matte. Color, developing: Close to 144A; edges, close to 199A. Color, developed: Close to 143B; at the nodes, close to 143C; surfaces exposed to sunlight, tinged with close to N199B.

Leaf description:

*Arrangement*.—Opposite, simple.

*Length*.—About 7.7 cm.

*Width*.—About 4.9 cm.

*Shape and aspect*.—Broadly ovate; slightly to moderately curled downward and slightly carinate.

*Apex*.—Short apiculate.

*Base*.—Truncate.

*Margin*.—Serrate; not lobed; slightly to non-undulate.

*Texture and luster, upper surface*.—Densely pubescent; rugose; slightly glossy.

*Texture and luster, lower surface*.—Densely pubescent; moderately rugose; matte.

*Venation pattern*.—Pinnate.

*Color*.—Developing leaves, upper surface: Close to 143A. Developing leaves, lower surface: Close to 143C. Fully expanded leaves, upper surface: Close to NN137A; venation, close to 144B. Fully expanded leaves, lower surface: Close to NN137D; venation, close to 145B.

*Petioles*.—Length: About 4 mm. Diameter: About 1.5 mm by 4 mm. Strength: Relatively strong. Texture and luster, upper surface: Smooth, glabrous; matte. Texture and luster, lower surface: Densely pubescent; matte. Color, upper surface: Close to 144A. Color, lower surface: Close to 145A.

Flower description:

*Flower arrangement and shape*.—Single campanulate flowers arranged on dense verticillasters; flowers face mostly outwardly. Flowering habit: Freely flowering habit with about 200 flowers developing per inflorescence and typically more than 40,000 flower buds and open flowers developing per plant during the flowering season.

*Fragrance*.—Faintly fragrant; sweet and pleasant.

*Natural flowering season*.—Long flowering period; plants flower continuously throughout the summer in The Netherlands.

*Flower longevity*.—Individual flowers last about seven days; flowers not persistent.

*Flower buds*.—Length: About 3 mm. Diameter: About 1.5 mm. Shape: Obovate. Texture and luster: Moderately to densely pubescent; matte. Color: Close to 84C; developing calyx, close to 144B and towards the apices, close to 146A.

*Inflorescence height* (*length*).—About 8.4 cm.

*Inflorescence diameter*.—About 2.3 cm.
*Flower diameter*.—About 4.5 mm by 5 mm.
*Flower height*.—About 7.5 mm.
*Throat diameter*.—About 1 mm.
*Tube length*.—About 4 mm.
*Tube diameter*.—About 1.5 mm.
*Petals*.—Quantity and arrangement: Five in a single whorl; upper petals broader than the lower petals; petals fused towards the base. Length, upper petals: About 6 mm. Length, lower petals: About 4 mm. Width, all petals: About 1.5 mm. Shape, all petals: Free part, broadly ovate with obtuse apices and entire and slightly undulate margins. Texture and luster, all petals, upper surface: Smooth, glabrous; slightly velvety; matte. Texture and luster, all petals, lower surface: Moderately pubescent; slightly glossy. Texture and luster, throat: Smooth, glabrous; matte. Texture and luster, tube: Smooth, glabrous; matte. Color, all petals: When opening and fully opened, upper surface: Close to a blend of 76B and 84C; venation, close to a blend of 76B and 84C; color does not change with subsequent development. When opening and fully opened, lower surface: Close to 76B; venation, close to 76B; color does not change with subsequent development. Throat: Close to N155A; venation, close to N155A. Tube: Close to 155B; venation, close to 155B.
*Sepals*.—Quantity and arrangement: Five arranged in a single whorl and lower half fused towards the base; calyx is campanulate in shape. Calyx length: About 3 mm. Calyx diameter: About 2 mm. Length: About 3 mm. Width: About 0.6 mm. Shape: Lanceolate. Apex: Narrowly acuminate. Margin: Entire. Texture and luster, upper surface: Smooth, glabrous; slightly glossy. Texture and luster, lower surface: Moderately pubescent; slightly glossy. Color: When opening and fully opened, upper surface: Close to 144C; apices, close to 143A. When opening and fully opened, lower surface: Close to 144B; apices, close to 146A.
*Peduncles*.—Length, primary peduncles: About 8 cm. Diameter, primary peduncles: About 2 mm. Aspect: Primary peduncles, upright; secondary peduncles, about 50° to 70° from primary peduncle axis. Strength: Relatively strong. Texture and luster: Densely pubescent; matte. Color: Close to 146C; surfaces exposed to sunlight, tinged with close to 200B.
*Pedicels*.—Length: About 2 mm. Diameter: About 0.25 mm. Aspect: About 45° from peduncle axis. Strength: Moderately strong; flexible. Texture and luster: Moderately pubescent; matte. Color: Close to 146C; surfaces exposed to sunlight, tinged with close to 177B.
*Reproductive organs*.—Stamens: Quantity per flower: About four. Filament length: About 6 mm. Filament color: Close to NN155D. Anther size: About 0.4 mm by 0.5 mm. Anther shape: Broadly elliptic; dorsifixed. Anther color: Close to 79A. Pollen amount: Scarce. Pollen color: Close to 156D. Pistils: Quantity per flower: One. Pistil length: About 7 mm. Stigma diameter: About 0.5 mm. Stigma shape: Cleft. Stigma color: Close to 76C. Style length: About 6.5 mm. Style color: Close to NN155D. Ovary color: Close to 143C.
*Seeds and fruits*.—To date, seed and fruit development has not been observed on plants of the new *Mentha*.

Pathogen & pest resistance: To date, plants of the new *Mentha* have not been noted to be resistant to pathogens and pests common to *Mentha* plants.

Field performance: Plants of the new *Mentha* have exhibited good field production performance and to be tolerant to rain, wind and to be suitable for USDA Hardiness Zones 4 through 9.

It is claimed:

1. A new and distinct *Mentha* plant named 'Allmefreshimp' as herein illustrated and described.

* * * * *